United States Patent [19]

Matier et al.

[11] 4,060,615
[45] Nov. 29, 1977

[54] 2-PIPERAZINYL-6,7-DIMETHOXYQUINAZOLINES

[75] Inventors: William Lesley Matier; John David Catt, both of Evansville, Ind.

[73] Assignee: Mead Johnson & Company, Evansville, Ind.

[21] Appl. No.: 659,059

[22] Filed: Feb. 18, 1976

[51] Int. Cl.$^2$ .................. A61K 31/505; C07D 403/04
[52] U.S. Cl. ............................. 424/251; 260/256.4 Q
[58] Field of Search .................. 260/256.4 Q; 424/251

[56] References Cited

U.S. PATENT DOCUMENTS

| | | | |
|---|---|---|---|
| 3,511,836 | 5/1970 | Hess ............................. | 260/256.4 Q |
| 3,669,968 | 6/1972 | Hess ............................. | 260/256.4 Q |
| 3,920,636 | 11/1975 | Takahashi et al. ........... | 260/256.4 Q |
| 3,935,213 | 1/1976 | Hess ............................. | 260/256.4 Q |

OTHER PUBLICATIONS

Pitts, "Postgraduate Medicine, Prazosin," 1975, pp. 117–127.

*Primary Examiner*—Donald G. Daus
*Assistant Examiner*—James H. Turnipseed
*Attorney, Agent, or Firm*—Robert H. Uloth; Robert E. Carnahan

[57] ABSTRACT

A series of novel 4-amino or 4-hydrazino-2-(substituted piperazinyl)-6,7-dimethoxyquinazolines is disclosed having antihypertensive and phosphodiesterase inhibiting properties. Piperazinyl substituents include cycloalkenylcarbonyl, cycloalkylcarbonyl, and methylcycloalkylcarbonyl. A representative embodiment of the invention is 4-amino-2-[4-(cyclopentylcarbonyl)-1-piperazinyl]-6,7-dimethoxyquinazoline.

19 Claims, No Drawings

2-PIPERAZINYL-6,7-DIMETHOXYQUINAZOLINES

BACKGROUND OF THE INVENTION

While a variety of agents are available for treatment of hypertension there, nevertheless, is a need for newer and improved antihypertensive agents to achieve better control of blood pressure in those subjects who do not respond satisfactorily or where drug associated side effects are seen.

This invention provides quinazoline compounds and pharmaceutically acceptable acid addition salts thereof having pharmacological properties making them particularly useful as antihypertensive agents. The quinazoline class of compounds of the instant invention structurally resemble the 2,4,6,7-tetrasubstituted quinazoline antihypertensive agents disclosed in U.S. Pat. No. 3,511,836. The compound "2-[4-(2-furoyl)-1-piperazin-1-yl]-4-amino-6,7-dimethoxyquinazoline," known as prazosin, is representative of the quinazolines of U.S. Pat. No. 3,511,836 and has been studied in the clinic. Although prazosin is apparently an effective antihypertensive agent, it is not altogether free from alpha-adrenoreceptor blocking activity or from undesirable side effects such as postural dizziness and orthostatic hypotension; N. E. Pitts, Postgraduate Medicine, Prazosin, pp. 117-127 (November, 1975).

The compounds of the instant invention are generally substantially more potent than prazosin as antihypertensives while, at the same time, exhibiting appreciably less alpha-adrenoreceptor blocking activity. Also, compared to prazosin, the instant compounds are more potent phosphodiesterase inhibitors and exhibit greater selectivity for the enzyme operative on the cyclic guanosine monophosphate (cycle GMP) substrate.

SUMMARY OF THE INVENTION

This invention is concerned with new quinazoline compounds, to a process for their preparation and pharmaceutical compositions thereof. The quinazolines possess valuable pharmacologic properties and another aspect of this invention relates to an antihypertensive process utilizing the new compounds. More particularly, the invention is especially concerned with 2-piperazinyl-6,7-di-methoxyquinazolines characterized by Formula I

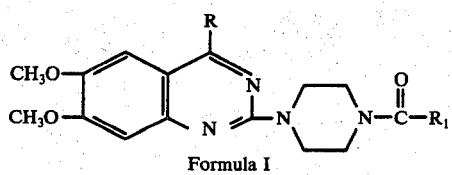

Formula I and pharmaceutically acceptable acid addition salts thereof wherein R is amino or hydrazino; and $R_1$ is cycloalkyl, or methylcycloalkyl, each having from 3 to 8 ring carbon atoms inclusive and cycloalkenyl having 4 to 8 carbon atoms inclusive.

It is to be understood that the term "cycloalkyl" as used herein includes cycloalkyl radicals containing 3 to 8 ring carbon atoms inclusive and encompasses such groups as cyclopropyl, cyclobutyl, cyclopentyl, cyclohexyl, cycloheptyl and cyclooctyl. The term "methylcycloalkyl" refers to the aforementioned cycloalkyl radicals containing from 3 to 8 ring carbons inclusive having a methyl substituent and encompasses such groups as 1-methylcyclopropyl, 1-methylcyclopentyl, 2-methylcyclopentyl, 3-methylcyclopentyl, 1-methylcyclohexyl, 2-methylcyclohexyl, 2-methylcycloheptyl, 4-methylcyclohexyl, and the like. By the term "cycloalkenyl," it is intended to refer to those having from 4 to 8 ring carbon atoms inclusive containing a single ring carbon-carbon double bond encompassing such groups as 1-cyclobutenyl, 1-cyclopentenyl, 2-cyclopentenyl, 3-cyclopentenyl, 1-cyclohexenyl, 2-cyclohexenyl, and the like.

The term "pharmaceutically acceptable" used herein to describe an acid addition salt of a compound of Formula I refers to those salts having anionic species of a variety of relatively non-toxic inorganic or organic acids. The anion does not contribute appreciably to the toxicity of the salt or to its pharmacological activity. Illustrative of such salts are those formed with acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzenesulfonic, p-toluenesulfonic, and related acids. Preparation of the mono-acid addition salts may be carried out in conventional manner by treating a solution or suspension of the free base in a reaction inert organic solvent with one chemical equivalent of the acid or if the di-acid addition salt is desired, at least two chemical equivalents of the acid. Conventional concentration or crystallization techniques are employed in isolating the salts.

A preferred group of quinazolines are those compounds of Formula I wherein R is limited to amino and $R_1$ is cycloalkyl.

According to the present invention, compounds of Formula I are prepared by reacting a quinazoline derivative of Formula II

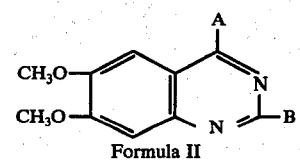

Formula II wherein substituent "A" is amino, hydrazino or halogen (preferably chlorine or bromine) and substituent "B" is halogen (preferably chlorine or bromine), piperazino, alkylthio of 1 to 4 carbon atoms inclusive or

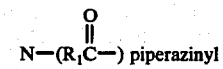

wherein $R_1$ is as defined above with a reactant of the group consisting of ammonia, $R_1COX$,

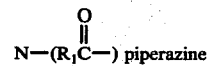

wherein $R_1$ is as defined above and "X" is halogen (preferably chlorine or bromine) in an aqueous or reaction inert organic solvent. Equimolar amounts of Formula II and $R_1COX$ or N—($R_1C$—)piperazine reactants are generally satisfactory, although, with ammonia, a substantial excess is preferred. The term "reaction inert solvent" as used herein refers to those organic solvents which themselves do not enter into the reaction including such polar solvents as the aliphatic alkanols (e.g., methanol, ethanol, isopropanol, isoamyl alcohol) tetrahydrofuran, dioxane, dimethylacetamide, dimethylformamide, and the like. When the reaction is complete, the solvent is removed by evaporation. The resulting residue, consisting of a salt of Formula I, stirred with a base such as ammonium hydroxide, sodium hydroxide, potassium hydroxide, sodium carbonate, potassium carbonate and then purified according to conventional crystallization techniques provides the Formula I free base.

The following reaction schemes of Equation 1-5 illustrate the various synthetic routes embodied in the preparation of the compounds of the instant invention according to the process discussed above.

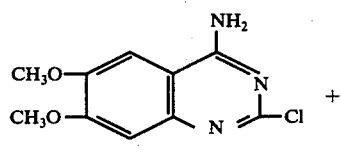

Equation 1

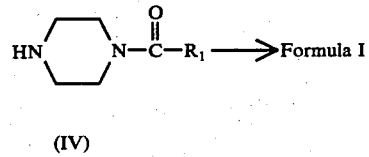

As depicted in equation 1 above, 2-chloro-4-amino-6,7-dimethoxyquinazoline of Formula III is reacted with an

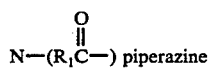

of Formula IV, wherein $R_1$ is as defined above, in an inert reaction solvent in an enclosed reactor at elevated temperatures. The reaction is generally complete in a period of 16 hours at a temperature ranging from 150°180° C. but can also be carried out at temperatures of 100°–180° C. for periods of 1 to 48 hours.

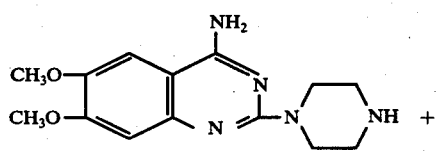

Equation 2

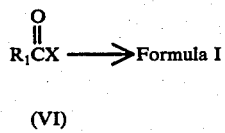

Equation 2 illustrates acylation of 2-piperazinyl-4-amino-6,7-dimethoxyquinazoline of Formula V with a carbonyl halide reactant of Formula VI wherein $R_1$ is as defined above and "X" is halogen (preferably bromine or chlorine). The reaction proceeds readily at room temperature in a reaction inert organic solvent and is essentially complete after the addition of the halogenide reactant. Representative inert organic solvents which may be employed include ether, benzene, toluene, acetonitrile, halogenated hydrocarbons such as chloroform, alkanols such as methanol or ethanol, dimethylformamide, dimethylsulfoxide, and the like. At least a molar equivalent of the carbonyl halide reactant (VI) is employed and the reaction is stirred for a period of 1 to 6 hours following addition. The products of Formula I are filtered from the reaction mixture or isolated by conventional techniques such as evaporation of the solvent and recrystallization of the residue from alkanol solvents such as methanol, ethanol, isopropanol, chloroform or the like.

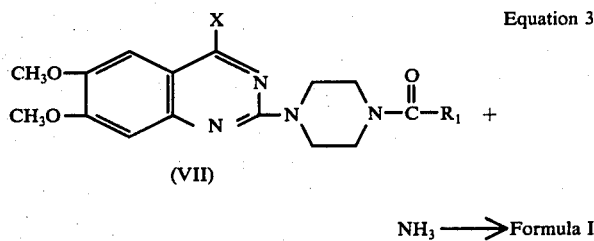

Equation 3

Equation 3 illustrates reaction of quinazolines of formula VII wherein $R_1$ is as defined above and substituent "X" is halogen, preferably chlorine or bromine, with ammonia. The reaction is carried out at 25°–150° C. for a period of 16 to 36 hours in a reaction inert solvent such as tetrahydrofuran or alcohol.

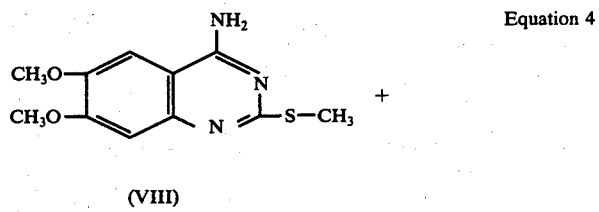

Equation 4

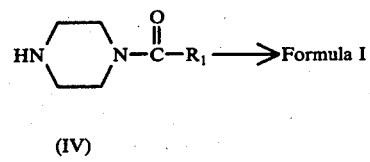

Equation 4 illustrates the reaction of a 2-methylmercaptoquinazoline of Formula VIII with an N—($R_1$CO)-piperazine of Formula IV. Preferably, the reaction is carried out in reaction inert solvent such as isoamyl alcohol at reflux temperature for a period of 16 hours.

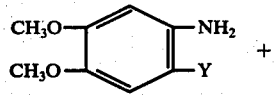

Equation 5

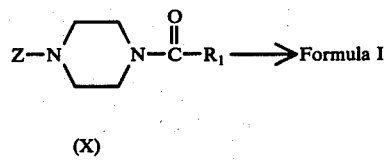

The compounds of Formula I can also be obtained according to the method disclosed in German Offenlegungschrift No. 2,457,911 which is illustrated by Equation 5. In this method, a 2-aminobenzonitrile or benzamidine of Formula IX is reacted with piperazine- 1-carboxamido ester or nitrile of Formula X in a reaction inert solvent. The reaction is carried out at a temperature of 50° to 180° C. in the presence of sodium hydride. In Formula IX, "Y" represents the radical —CN or —C(=NH)NH$_2$ and in Formula X, "Z" represents the radical —CN, —C(=NH)—OR$_3$ or —C(=NH)SR$_3$ wherein R$_3$ is an alkyl radical of 1 to 4 carbon atoms inclusive.

The 2-piperazinyl-6,7-dimethoxyquinazolines characterized by Formula I are effective antihypertensive agents having substantially less alpha-adrenergic blocking activity than prazosin. They also are phosphodiesterase inhibitors exhibiting cyclic-GMP enzyme selectivity. These desirable effects can be readily demonstrated in standard in vitro and in vivo pharmacological tests. For instance, in the spontaneous hypertensive rat, oral administration of 0.4 mg./kg. body weight of 4-amino-2-[4-(cyclopentylcarbonyl)piperazinyl]-6,7-dimethoxyquinazoline provides a 50 mm Hg reduction in blood pressure. To obtain a similar reduction in blood pressure with prazosin, a dose of 1.8 mg./kg. body weight is required. This following table provides a pharmacological profile of 4-amino-2-[4-(cyclopentylcarbonyl)piperazinyl]-6,7-dimethoxyquinazoline wherein activity is expressed as a multiple of the activity of the reference standard prazosin taken as unity.

TABLE I

Activity of 4-Amino-2-[4-(cyclopentylcarbonyl)-1-piperazinyl]-6,7-dimethoxyquinazoline Relative to Prazosin (=1)

| | Formula I (R = NH$_2$, R$_1$ = cyclopentyl) Times Prazosin |
|---|---|
| Antihypertensive potency in spontaneous hypertensive rats | 4.25 |
| Alpha-adrenergic blocking potency: in vivo (intravenous administration) in the rat versus phenylephrine | 0.47 |
| Antihypertensive/alpha blocking ratio based on: in vivo alpha block | 9.0 |
| Inhibition of cyclic nucleotide phosphodiesterase in rat heart based on in vitro determination of inhibitor constants using cyclic adenosine monophosphate or cyclic guanosine monophosphate: | |
| potency | 2.0 – 2.5 |
| selectivity for the cyclic GMP enzyme | 2.0 – 3.5 |

As seen in the above table, 4-amino-2-[4-(cyclopentylcarbonyl)-1-piperazinyl]-6,7-dimethoxyquinazoline has an antihypertensive/alpha in vivo blocking ratio of 9.0 compared to prazosin. With respect to antihypertensive utility this is considered a very favorable ratio since it is indicative of a reduction in blood pressure without significant involvement of the alpha adrenergic system.

One of the most undesirable side effects encountered in antihypertensive therapy is postural hypotension which results from hemodynamic alterations induced by change from supine to erect position. Postural hypotension is generally manifested in the clinic by dizziness and/or faintness.

A useful animal model predictive of postural hypotension in man is the "dog tilt test"; refer to J. W. Constantine, et al., Am. J. Physiol. 221, No. 6, 1681–1685 (1971). In this test, anesthetized dogs monitored for blood pressure are secured to a specially constructed table on which they are rapidly tilted to a position 80°–90° from the horizontal in the head-up position for 1–2 minutes. Each animal is positioned with respect to the fulcrum of the table so that the heart is approximately in the same horizontal plane in both supine and tilted positions. Prior to drug (control), tilting the animal causes an initial fall in blood pressure which is followed by a compensatory rise to or slightly above the pre-tilt level. Ten minutes after the control tilt, the drug is administered intraveneously over a 3-minute period and tilt repeated. Impairment of reflex compensation to the upright position is considered to be drug induced and indicative of possible postural hypotension in humans.

Data provided by the foregoing "dog tilt test" establishes that, compared to prazosin, 4-amino-2-[4-(cyclopentylcarbonyl)-1-piperazinyl]-6,7-dimethoxyquinazoline has only 0.36 of the potential for postural hypotension at equi-antihypertensive doses.

The process of the instant invention for treating hypertension is carried out by systemically administering to a mammal in need of such treatment such as those having hypertension or predisposed thereto an antihypertensive effective amount of a 2-piperazinyl-6,7-dimethoxyquinazoline characterized by Formula I or a pharmaceutically acceptable acid addition salt thereof. By systemic administration, it is intended to include both oral and parenteral routes. Examples of parenteral administration are intramuscular, intravenous, intraperitoneal, rectal, and subcutaneous administration. The dosage will vary with the form of administration and the particular compound chosen however, from about 0.001 to 50 milligrams per kilogram of body weight of the mammal of a 2-piperazinyl-6,7-dimethoxyquinazoline characterized by Formula I administered in effective single or multiple dosage units is generally satisfactory. In accordance with conventional clinical practice, an antihypertensive agent of Formula I is administered at a dosage substantially less than the dose of the compound which is thought to be effective. Thereafter, the dosage is increased by small increments until the optimum antihypertensive effect under the circumstances is reached. At effective antihypertensive dosage levels, the compounds of this invention are substantially free of postural hypotension and those harmful or deleterious side effects generally associated with alpha-adrenergic blockade.

In carrying out the antihypertensive process, the active ingredient of Formula I and pharmaceutically acceptable acid addition salts thereof may be administered orally in such forms as tablets, dispersable powders, granules, capsules, syrups and elixirs and parenterally as solutions, suspensions, dispersions, emulsion, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated or coated by known techniques to delay disintegration and absorption in the gastrointestinal tract and thereby provide a sustained action over a longer period. Similarly, suspensions, syrups, and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectible compositions are formulated as known in the art and may contain appropriate dispersing or wetting agents and suspending agents identical or similar to those mentioned above.

The following examples are given by way of illustration and are not to be construed as limiting the invention in any way inasmuch as many variations of the invention are possible within the spirit of the invention.

EXAMPLE 1

4-Amino-2-[4-(cyclopentylcarbonyl)-1-piperazinyl]-6,7-dimethoxyquinazoline a. A mixture of N-(cyclopentylcarbonyl)piperazine (3.6 g., 0.02 mole) and 2-chloro-4-amino-6,7-dimethoxyquinazoline (4.79 g., 0.02 mole) in 50 ml. of absolute ethanol is heated in an enclosed reactor at 170° C. for a period of 16 hours. The reaction mixture is cooled, filtered and insolubles triturated with 100 ml. of concentrated ammonium hydroxide to provide the free base. The insoluble product is collected and crystallized from methanol to afford analytically pure 4-amino-2-[4-(cyclopentylcarbonyl)-1-piperazinyl]-6,7-dimethoxyquinazoline, m.p. 256.0°–259.0° (corr.).

Analysis. Calcd. for $C_{20}H_{27}N_5O_3$ (percent): C, 62.32; H, 7.06; N, 18.17. Found (percent): C, 62.06; H, 7.24; N, 17.99.

Example 1(a) illustrates the procedure of aforementioned Equation 1 while the following Examples 1 (b–e) illustrate procedures of Equations 2–5, respectively, for the preparation of 4-amino-2-[4-(cyclopentylcarbonyl)-1-piperazinyl]-6,7-dimethoxyquinazoline.

b. Cyclopentylcarbonyl chloride (0.1 mole) is added to 0.1 mole of 4-amino-2-(1-piperazinyl)-6,7-dimethoxyquinazoline in 300 ml. of methanol with vigorous stirring at room temperature. Stirring is continued for a period of 2 to 6 hours and the product is isolated according to the procedure of Example 1(a) to provide 4-amino-2-[4-(cyclopentylcarbonyl)-1-piperazinyl]-6,7-dimethoxyquinazoline. If the hydrochloride salt is desired, the base treatment is omitted and evaporation of the solvent provides 4-amino-2-[4-(cyclopentylcarbonyl)-piperazinyl]-6,7-dimethoxyquinazoline hydrochloride, m.p. 279°–280° C. (dec.)(corr.) crystallized from methanol-isopropanol.

Analysis. Calcd. for $C_{20}H_{27}N_5O_3 \cdot HCl$ (percent): C, 56.93; H, 6.69; N, 16.60. Found (percent): C, 56.65; H, 6.89; N, 16.44.

c. A mixture of anhydrous ammonia and 4-chloro-2-[4-(cyclopentylcarbonyl)-1-piperazinyl]-6,7-dimethoxyquinazoline in 100 ml. of tetrahydrofuran is heated at 100° C. for a period of 16 to 24 hours and the product isolated according to the procedure of Example 1(a) to provide 4-amino-2-[4-(cyclopentylcarbonyl)-1-piperazinyl]-6,7-dimethoxyquinazoline.

d. A mixture of 4-amino-2-methylmercapto-6,7-dimethoxyquinazoline (0.1 mole) and from 0.1 to 0.15 mole of N-(cyclopentylcarbonyl)piperazine in 150 ml. of isoamyl alcohol is refluxed for a period of 8 to 24 hours. The solvent is evaporated and residual material, treated according to procedure of Example 1(a), provides 4-amino-2-[4-(cyclopentylcarbonyl)-1-piperazinyl]-6,7-dimethoxyquinazoline.

e. Ethyl-4-(cyclopentylcarbonyl)piperazin-1-yl-formamidate hydrochloride (0.01 mole) is added to a solution of 4,5-dimethoxy-2-aminobenzonitrile (0.01 mole) in 30 ml. of $N_1N$-dimethylformamide. Sodium hydride (0.02 mole of a 56% suspension in mineral oil) is added and the mixture stirred 0.5 hr. at room temperature and then at 100° C. for a period of 12 hr. When the reaction period is complete, water is added providing 4-amino-2-[4-cyclopentylcarbonyl)-1-piperazinyl]-6,7-dimethoxyquinazoline.

EXAMPLE 2

4-Amino-2-[4-(cyclopropylcarbonyl)-1-piperazinyl]-6,7-dimethoxyquinazoline

N-(Cyclopropylcarbonyl)piperazine (3.08 g., 0.02 mole) and 2-chloro-4-amino-6,7-dimethoxyquinazoline (4.74 g., 0.02 mole) are reacted according to the procedure of Example 1(a). The crude product crystallized from ethanol affords analytically pure 4-amino-2-[4-(cyclopropylcarbonyl)-1-piperazinyl]-6,7-dimethoxyquinazoline, m.p. 283.5°–285.5° C. (corr.).

Analysis. Calcd. for $C_{18}H_{23}N_5O_3$ (percent): C, 60.49; H, 6.49; N, 19.59. Found (percent): C, 60.56; H, 6.46; N, 19.41.

EXAMPLE 3

4-Amino-2-[4-(cyclohexylcarbonyl)-1-piperazinyl]-6,7-dimethoxyquinazoline

N-(Cyclohexylcarbonyl)piperazine (5.9 g., 0.03 mole) and 2-chloro-4-amino-6,7-dimethoxyquinazoline (7.2 g., 0.03 mole) are reacted according to the procedure of Example 1(a). The crude product crystallized from methanol affords analytically pure 4-amino-2-[4-(cyclohexylcarbonyl)-1-piperazinyl]-6,7-dimethoxyquinazoline, m.p. 223°–225° C., resolidifying and remelting at 248.0°–250.0° C. (corr.)

Analysis. Calcd. for $C_{21}H_{29}N_5O_3$ (percent): C, 63.14; H, 7.32; N, 17.53. Found (percent): C, 63.07; H, 7.43; N, 17.63.

EXAMPLE 4

4-Amino-2-[4-(cyclopenten-1-ylcarbonyl)-piperazinyl]-6,7-dimethoxyquinazoline

N-(1-cyclopenten-1-ylcarbonyl)piperazine (1.8 g., 0.01 mole) and 2-chloro-4-amino-6,7-dimethoxyquinazoline (2.4 g., 0.01 mole) are reacted according to the procedure of Example 1(a). The isolated product crystallized from methanol affords analytically pure 4-amino-2-[4-(1-cyclopenten-1-ylcarbonyl)piperazinyl]-6,7-dimethoxyquinazoline, m.p. 256.5°–258.0° C. (corr.).

Analysis. Calcd. for $C_{20}H_{25}N_5O_3$ (percent): C, 62.65; H, 6.57; N, 18.26. Found (percent): C, 65.23; H, 6.56; N, 18.42.

EXAMPLE 5

4-Amino-2-[4-(3-cyclopentenylcarbonyl)-1-piperazinyl]-6,7-dimethoxyquinazoline

N-(3-cyclopentenylcarbonyl)piperazine (2.7 g., 0.015 mole) and 2-chloro-4-amino-6,7-dimethoxyquinazoline (3.6 g., 0.015 mole) are reacted according to the procedure of Example 1(a). The crude product crystallized from methanol affords analytically pure 4-amino-2-[4-

(3-cyclopentenylcarbonyl)-1-piperazinyl]-6,7-dimethoxyquinazoline, m.p. 215.5°–217.5° C. (corr.).

Analysis. Calcd. for $C_{20}H_{25}N_5O_3$ (percent): C, 62.65; H, 6.57; N, 18.26. Found (percent): C, 62.35; H, 6.72; N, 18.21.

EXAMPLE 6

4-Amino-2-[4-(3-cyclohexenylcarbonyl)-1-piperazinyl]-6,7-dimethoxyquinazoline

N-(3-cyclohexenylcarbonyl)piperazine (7.65 g., 0.04 mole) and 2-chloro-4-amino-6,7-dimethoxyquinazoline (9.6 g., 0.04 mole) are reacted according to the procedure of Example 1(a). The crude product crystallized from methanol affords analytically pure 4-amino-2-[4-(3-cyclohexenylcarbonyl)-1-piperazinyl]-6,7-dimethoxyquinazoline, m.p. 211°–213° C. resolidifying and melting at 234.0° –236.0°C. (corr.).

Analysis. Calcd. for $C_{21}H_{27}N_5O_3$ (percent): C, 63.46; H, 6.85; N, 17.62. Found (percent): C, 63.18; H, 6.80; N, 17.63.

EXAMPLE 7

4-Amino-2-[4-(cyclobutylcarbonyl)-1-piperazinyl]-6,7-dimethyxyquinazoline Hydrochloride N-(Cyclobutylcarbonyl)piperazine (0.02 mole) and 2-chloro-4-amino-6,7-dimethoxyquinazoline (0.02 mole) are reacted according to the procedure of Example 1(a). When reaction is complete, the solvent is removed and the residue crystallized from methanolisopropanol to provide analytically pure 4-amino-2-[4-(cyclobutylcarbonyl)-1-piperazinyl]-6,7-dimethoxyquinazoline hydrochloride hydrate, m.p. 267°–268° C. (dec.)(corr.).

Analysis. Calcd. for $C_{19}H_{25}N_5O_3.HCl.\frac{1}{4}H_2O$ (percent): C, 55.33; H, 6.48; N, 16.98. Found (percent): C, 55.49; H, 6.75; N, 16.62.

EXAMPLE 8

4-Amino-2-[4-(cycloheptylcarbonyl)-1-piperazinyl]-6,7-dimethoxyquinazoline Hydrochloride N-(Cycloheptylcarbonyl)piperazine (0.02 mole) and 2-chloro-4-amino-6,7-dimethoxyquinazoline (0.02 mole) are reacted according to the procedure of Example 7. Crystallization of the product from methanol-isopropanol provides analytically pure 4-amino-2-[4-(cycloheptylcarbonyl)-1-piperazinyl]-6,7-dimethoxyquinazoline hydrochloride, m.p. 278°–279° C. (corr.).

Analysis. Calcd. for $C_{22}H_{31}N_5O_3.HCl$ (percent): C, 58.72; H, 7.17; N, 15.56. Found (percent): C, 58.73; H, 7.39; N, 15.44.

EXAMPLE 9

Following the procedure of Example 1 but employing an equimolar amount of:

N-(2-cyclopentenylcarbonyl)piperazine,
N-(1-cyclohexen-1-ylcarbonyl)piperazine,
N-(1-cyclohexen-1-ylcarbonyl)piperazine,
N-(cyclooctylcarbonyl)piperazine,
N-(2-methylcyclopentylcarbonyl)piperazine,
N-(1-methylcyclopentylcarbonyl)piperazine,
N-(1-methylcyclohexylcarbonyl)piperazine, in place of N-(cyclopentylcarbonyl)piperazine, there is produced:

a. 4-amino-2-[4-(2-cyclopentenylcarbonyl)1-piperazinyl]-6,7-dimethoxyquinazoline,
b. 4-amino-2-[4-(1-cyclohexen-1-ylcarbonyl)-1-piperazinyl]-6,7-dimethoxyquinazoline,
c. 4-amino-2-[4-(cyclooctylcarbonyl)-1-piperazinyl]-6,7-dimethoxyquinazoline,
d. 4-amino-2-[4-(2-methylcyclopentylcarbonyl)-1-piperazinyl]-6,7-dimethoxyquinazoline,
e. 4-amino-2-[4-(1-methylcyclopentylcarbonyl)-1-piperazinyl]-6,7-dimethoxyquinazoline,
f. 4-amino-2-[4-(1-methylcyclohexylcarbonyl)-1-piperazinyl]-6,7-dimethoxyquinazoline.

EXAMPLE 10

4-Hydrazino-2-[4-(cyclopentylcarbonyl)-1-piperazinyl]-6,7-dimethoxyquinazoline Hydrochloride N-(Cyclopentylcarbonyl)piperazine (0.02 mole) and 2-chloro-4-hydrazino-6,7-dimethoxyquinazoline (0.02 mole) reacted according to the procedure of Example 7 provides 4-hydrazino-2-[4-(cyclopentylcarbonyl)-1-piperazinyl]-6,7-dimethoxyquinazolinehydrochloride, m.p. 282°–284° C.

EXAMPLE 11

Suspensions

A suspension of 4-amino-2-[4-(cyclopentylcarbonyl)-1-piperazinyl]-6,7-dimethoxyquinazoline or a pharmaceutically acceptable salt thereof is prepared with the following ingredients:
Active ingredient: 20 g.
Sucrose, U.S.P.: 400 g.
Sorbitol, U.S.P.: 100 g.
Bentonite: 20 g.
Flavors, q.s.
Water, distilled to make 1 liter Each milliliter of the suspension contains approximately 20 mg. of the active ingredient.

EXAMPLE 12

Tablets

The following ingredients are blended in the proportion by weight indicated according to conventional pharmaceutical techniques to provide a tablet base:
Lactose: 79
Corn Starch: 10
Talcum: 6
Tragancanth: 4
Magnesium Stearate: 1

This tablet base is blended with sufficient 4-amino-2-[4-(cyclopentylcarbonyl)-1-piperazinyl]-6,7-dimethoxyquinazoline or a pharmaceutically acceptable salt thereof to provide tablets containing 0.1, 0.25, 0.5, 1, 2.5, 5, 7.5, 10, 25, and 50 mg. of active ingredient; formed in a tablet of the desired size in a conventional tablet press.

EXAMPLE 13

Dry Filled Capsules

The following ingredients are blended in a conventional manner in the proportion by weight indicated.
Lactose, U.S.P.: 50
Starch: 5
Magnesium stearate: 2

Sufficient 4-amino-2-[4-(cyclopentylcarbonyl)-1-piperazinyl]-6,7-dimethoxyquinazoline or a pharmaceutically acceptable salt thereof is added to the blend to provide capsules containing 0.1, 0.25, 0.5, 1, 2.5, 5, 7.5, 10, 25, and 50 mg. of active ingredient, and filled into hard gelatin capsules of a suitable size.

What is claimed is:

1. A compound having the formula

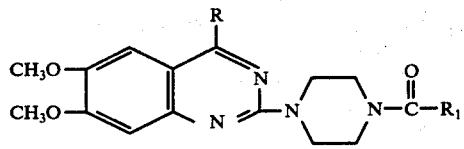

or a pharmaceutically acceptable salt thereof wherein
R is amino or hydrazino;
$R_1$ is cycloalkyl having 3 to 8 ring carbon atoms inclusive and cycloalkenyl having 4 to 8 ring carbon atoms inclusive.

2. The compound defined in claim 1 which is 4-amino-2-[4-(cyclopentylcarbonyl)-1-piperazinyl]-6,7-dimethoxyquinazoline.

3. The compound defined in claim 1 which is 4-amino-2-[4-(cyclopentylcarbonyl)-1-piperazinyl]-6,7-dimethoxyquinazoline hydrochloride.

4. The compound defined in claim 1 which is 4-amino-2-[4-(cyclopropylcarbonyl)-1-piperazinyl]-6,7-dimethoxyquinazoline.

5. The compound defined in claim 1 which is 4-amino-2-[4-(cyclohexylcarbonyl)-1-piperazinyl]-6,7-dimethoxyquinazoline.

6. The compound defined in claim 1 which is 4-amino-2-[4-(1-cyclopenten-1-ylcarbonyl)piperazinyl]-6,7-dimethoxyquinazoline.

7. The compound defined in claim 1 which is 4-amino-2-[4-(3-cyclopentenylcarbonyl)-1-piperazinyl]-6,7-dimethoxyquinazoline.

8. The compound defined in claim 1 which is 4-amino-2-[4-(3-cyclohexenylcarbonyl)-1-piperazinyl]-6,7-dimethoxyquinazoline.

9. The compound defined in claim 1 which is 4-amino-2-[4-(cyclobutylcarbonyl)-1-piperazinyl]-6,7-dimethoxyquinazoline.

10. The compound defined in claim 1 which is 4-amino-2-[4-(cyclobutylcarbonyl)-1-piperazinyl]-6,7-dimethoxyquinazoline hydrochloride.

11. The compound defined in claim 1 which is 4-amino-2-[4-(cycloheptylcarbonyl)-1-piperazinyl]-6,7-dimethoxyquinazoline.

12. The compound defined in claim 1 which is 4-amino-2-[4-(cycloheptylcarbonyl)-1-piperazinyl]-6,7-dimethoxyquinazoline hydrochloride.

13. A process for treating hypertension which comprises systemically administering to a mammal in need of said treatment an antihypertensive effective amount of a compound having the formula

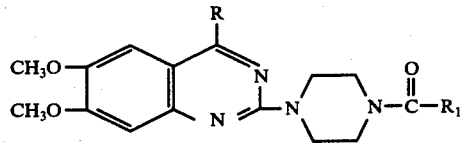

or a pharmaceutically acceptable salt thereof wherein
R is amino or hydrazino;
$R_1$ is cycloalkyl having 3 to 8 ring carbon atoms inclusive and cycloalkenyl having 4 to 8 ring carbon atoms inclusive.

14. The process of claim 13 wherein said compound is 4-amino-2-[4-(cyclopentylcarbonyl)-1-piperazinyl]-6,7-dimethoxyquinazoline.

15. The process of claim 13 wherein said compound is 4-amino-2-[4-(cyclopentylcarbonyl-1-piperazinyl]-6,7-dimethoxyquinazoline hydrochloride.

16. A pharmaceutical composition in dosage unit form adapted for the systemic administration to a mammal comprising a dose of from 0.001 to 50 mg. per kilogram of body weight of said mammal of a compound having the formula

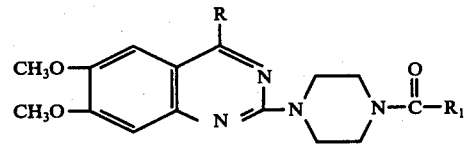

or a pharmaceutically acceptable salt thereof wherein
R is amino or hydrazino;
$R_1$ is cycloalkyl having 3 to 8 ring carbon atoms inclusive and cycloalkenyl having 4 to 8 ring carbon atoms inclusive.

17. The composition of claim 16 wherein said compound is 4-amino-2-[4-(cyclopentylcarbonyl)-1-piperazinyl]-6,7-dimethoxyquinazoline.

18. The compound of claim 16 wherein said compound is 4-amino-2-[4-(cyclopentylcarbonyl)-1-piperazinyl]-6,7-dimethoxyquinazoline hydrochloride.

19. The compound 4-amino-6,7-dimethoxy-2-[4-[(1-methylcyclohexyl)carbonyl]-1-piperazinyl]quinazoline.

* * * * *